United States Patent [19]

Ege

[11] Patent Number: 5,223,124
[45] Date of Patent: Jun. 29, 1993

[54] METHOD FOR IMMOBILIZING A POLYPEPTIDE IN A POLYMER AND A MEMBRANE PRODUCED THEREBY

[75] Inventor: Henrik Ege, Soborg, Denmark

[73] Assignee: Novo Nordisk A/S, Bagsvaerd, Denmark

[21] Appl. No.: 543,770

[22] PCT Filed: Feb. 3, 1989

[86] PCT No.: PCT/DK89/00019
§ 371 Date: Sep. 5, 1990
§ 102(e) Date: Sep. 5, 1990

[87] PCT Pub. No.: WO89/07139
PCT Pub. Date: Aug. 10, 1989

[30] Foreign Application Priority Data
Feb. 5, 1988 [DK] Denmark ............................. 614/88

[51] Int. Cl.⁵ ............................................. G01N 27/26
[52] U.S. Cl. .................................... 204/418; 204/403;
204/153.12; 435/177; 435/178; 435/180;
435/817
[58] Field of Search ............... 435/177, 178, 180, 817;
427/213.31, 213.33; 204/403, 418, 153.12

[56] References Cited

U.S. PATENT DOCUMENTS

| | | | |
|---|---|---|---|
| 4,094,744 | 6/1978 | Hartdegen et al. | 195/63 |
| 4,237,229 | 12/1980 | Hartdegen et al. | 435/180 |
| 4,407,957 | 10/1983 | Lim | 435/178 |
| 4,791,061 | 12/1988 | Sumino et al. | 435/177 |
| 4,871,716 | 10/1989 | Longo et al. | 435/177 |

FOREIGN PATENT DOCUMENTS

| | | |
|---|---|---|
| 0216577 | 4/1987 | European Pat. Off. |
| 0222289 | 5/1987 | European Pat. Off. |
| 0280212 | 8/1988 | European Pat. Off. |

OTHER PUBLICATIONS
Sharma et al., Chem. Abstracts, vol. 103, p. 320, abstract No. 200839n (1985).

Primary Examiner—John Niebling
Assistant Examiner—Bruce F. Bell
Attorney, Agent, or Firm—Steve T. Zelson; Elias J. Lambiris

[57] ABSTRACT

The present invention relates generally to the immobilization or incorporation of polypeptides, especially enzymes or other bioactive polypeptides into polymeric matrixes, especially polyurethane, membranes produced by said polymers, and the utilization of such membranes in biosensors. A preferred type of biosensor is the needle sensor designed for in vivo monitoring of glucose which comprises a core platinum anode (2) coated with an insulating lacquer (3), the anode (2) is situated inside a stainless steel reference cathode (4) which is insulated from the anode (2) by a layer of epoxy resin (5). At one end, of the tip, the electrode (1) has a detection surface (6), which is in an acute angle to the general direction of the electrode (1). At the other end, the base, the electrode (2) is provided with terminals (7) and (8) for the anode (2) and cathode (4), respectively. The terminals (7) and (8) are soldered to leads (9) and (10), respectively, which are connected to instrumentation used when performing measurements.

12 Claims, 2 Drawing Sheets

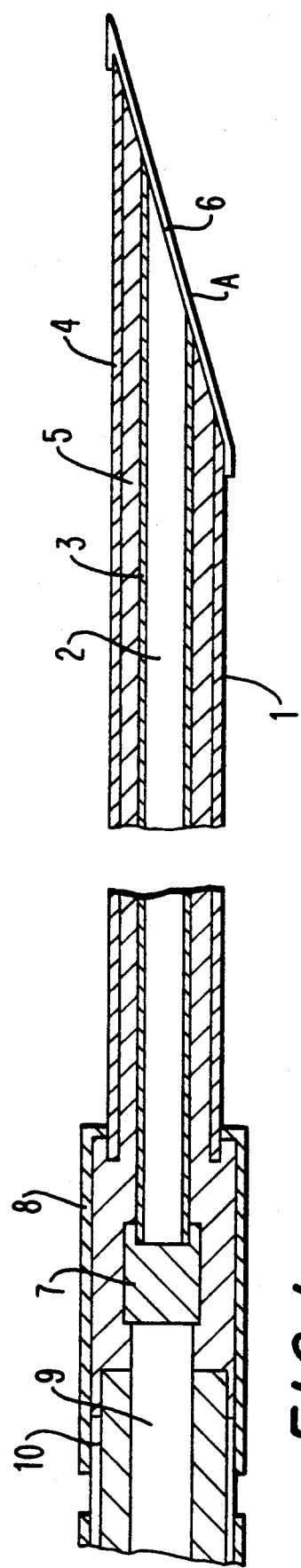
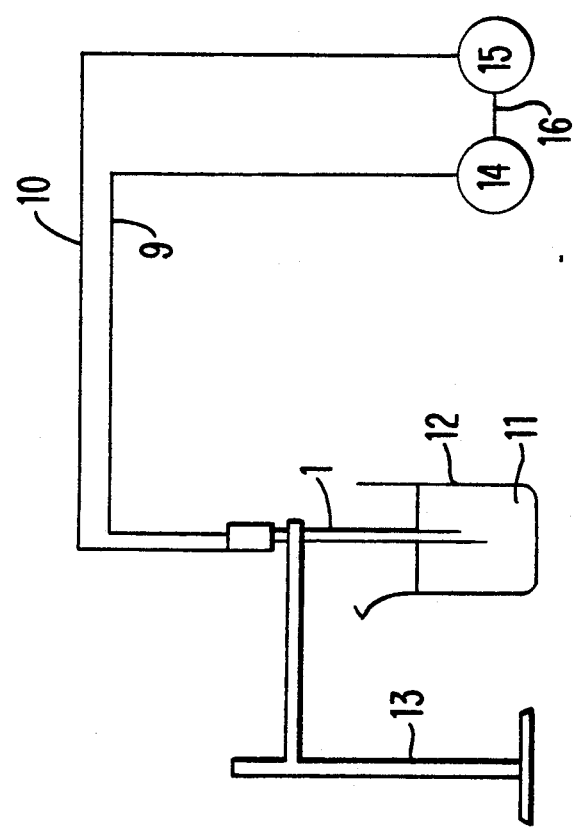
FIG. 1
FIG. 2

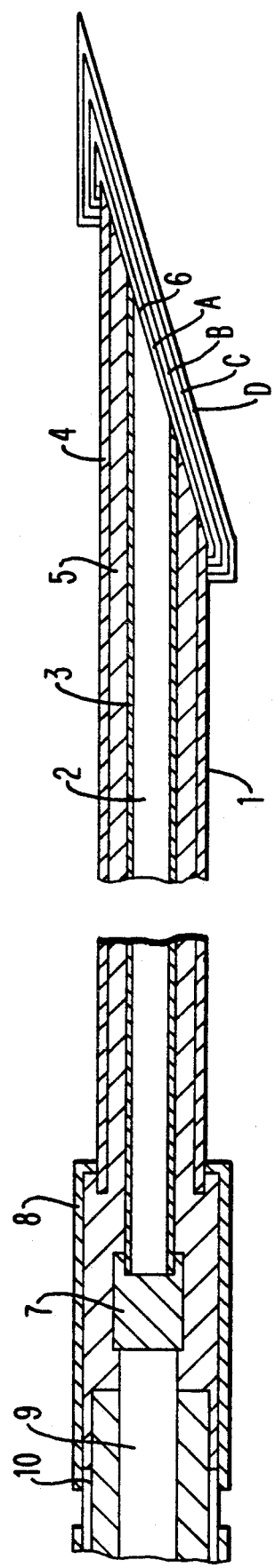

METHOD FOR IMMOBILIZING A POLYPEPTIDE IN A POLYMER AND A MEMBRANE PRODUCED THEREBY

TECHNICAL FIELD

The present invention relates generally to the immobilization or incorporation of polypeptides, especially enzymes or other bioactive polypeptides into polymeric matrixes, membranes produced by said polymers, and the utilization of such membranes in biosensors or electrochemical sensors.

BACKGROUND OF THE INVENTION

In the past enzymes have been utilized industrially as catalysts, particularly in the fermentation industry, and the like. In general, the enzymes were dissolved or dispersed in various aqueous media for promoting a chemical reaction. After completion of the reaction the enzyme is not recovered, but discarded. However, in recent years enzyme immobilization techniques have been developed, which enable repeated or continuous use of enzymes in a stable and active immobilized state, whereby the areas of use for enzymes have been rapidly expanded, for example in the process industry, and to analyses such as EIA (Enzyme Immuno Assay), and ELISA (Enzyme Linked Immuno Sorbent Assay).

The measurements of concentrations of various components in blood or other body fluids are very important for clinical diagnosis, and consequently a great number of improvements or developments in various kinds of quantitative measurements have been achieved.

Among these achievements the development of enzyme sensors has received attention, and a number have been proposed which are able to effect rapid and continuous measurements by employing membranes wherein enzymes have been immobilized.

Information concerning the development of biosensors, their advantages and shortcomings may be found in the following review articles: "Biosensors, Fundamentals and Applications" Eds. Turner, Karube and Wilson, Oxford University Press (1987) especially pages 409-424; Davis, Biosensors, 2 (1986) 101-124 and Churchouse et al., Biosensors, 2 (1986) 325-342, which are hereby incorporated by reference.

Biosensors are typical examples of sensors utilizing enzymes immobilized in membranes for the measurement of chemical substances. Such a biosensor comprises an enzyme immobilized in a membrane and a transducer adapted to detect substances consumed or produced in the membrane, which generates an electrical signal upon detection of such a substance. In this case the enzyme immobilized in the membrane serves to discriminate a specific chemical substance to be measured, and causes a change in quantity of a material which corresponds to a change in the chemical substance and which is able to be detected by the transducer.

Among such biosensors there are known those which employ glucose oxidase for the measurement of glucose.

Glucose oxidase acts to decompose glucose according to the following reaction:

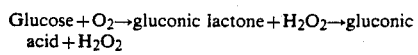

Glucose+$O_2$→gluconic lactone+$H_2O_2$→gluconic acid+$H_2O_2$     (1)

Accordingly it is possible to measure the concentration (activity) of glucose by detecting the quantity of oxygen consumed, the quantity of hydrogen peroxide produced, or the reduction in pH obtained in the above reaction inside the membrane.

In the enzyme sensors fabricated in the early years of this development, an enzyme immobilized in a membrane was physically or chemically applied to a sensitive portion of an enzyme sensor which is adapted to convert physical or chemical quantities such as temperature, ion activity, gas activity or the like into electrical signals. Now, however, with miniaturization of enzyme sensors, it has become necessary to selectively form a membrane containing an immobilized enzyme on the surface of a limited area of a sensitive portion of a sensor.

In order for these membranes to be functional in the biosensor in question they should fulfil a number of requirements depending on the type and nature of said biosensor.

Of such requirements a number may be mentioned, notably, stability in biological fluids, response over a clinically useful range, high selectivity, independence from variations in interfering substances, fast response, robustness, small size, stir independence, and biocompatibility.

In order to fulfil such requirements sensors have been proposed which comprise multi-layer membranes of substantial complexity. In the sensors which have been proposed in the past, the immobilization has been achieved by chemically binding the enzyme to the polymeric matrix. Such sensors are difficult and costly to produce in demanding considerable skill in the production, and the number of sensors that must be discarded is relatively large.

Specific examples of biosensors are described in the following patents and patent applications.

U.S. Pat. Nos. 4,484,987 and 4,650,547 to Gough describe membranes useful in sensor devices, sensor devices, and the use of the membranes for determining a dissolved component in the presence of a gas reactive to said component, such as glucose and oxygen in a solution.

German Patent Publication No. DE-A1-3335691 to Hitachi Ltd. discloses a urea electrode with a membrane comprising immobilized enzyme, which membrane is based on cross-linked albumin and treated with ethylenediamine in order to introduce and increase the number of amino groups, whereby an increased permeability for ammonium ions is achieved.

In German Patent Publication No. DE-A1-2625544 a process for immobilizing biological material is disclosed, by which process the biological material is covalently bound to free isocyanate groups in a polyurethane polymer through reactive amino groups in the biological material.

BRIEF DESCRIPTION OF THE INVENTION

It is object of this invention to provide a simple and reliable method of immobilizing polypeptides, especially enzymes or other bioactive polypeptides into polymeric matrices by physical entrapment without covalently binding the polypeptide to the polymeric matrix, whereby the activity of the polymer could be decreased.

A further object of the present invention is to provide for membranes produced by said polymeric matrices.

A still further object is related to the utilization of such membranes in biosensors.

Yet another object of the invention is to provide for a robust and reliable high quality biosensor incorporating membranes produced according to the method mentioned above.

The invention is described in further detail in the following detailed description and in connection with the appended examples and figures.

BRIEF DESCRIPTION OF THE DRAWING

In the drawings FIG. 1 shows a longitudinal cross section of a single layer membrane needle electrode according to the invention, FIG. 2 shows an electrode according to the invention as used in a measuring set up, and FIG. 3 shows a cross section of a multi-layer membrane electrode of the invention corresponding to the longitudinal cross section of a single layer membrane needle electrode in FIG. 1.

DETAILED DESCRIPTION OF THE INVENTION

As indicated above the invention in one of its aspects relates to a method for immobilizing a polypeptide such as an enzyme in a polymeric matrix comprising the following steps:

a) adding said polypeptide and a permeability modifying agent to an aqueous dispersion of a polymer to produce an aqueous dispersion wherein said polypeptide is dissolved;

b) forming said dispersion into one or more bodies of a desired shape;

c) leaving said shaped body for a period of time from about 5 minutes to about 200 minutes at room temperature for drying.

According to the invention a simple and reliable method of immobilizing a polypeptide, such as an enzyme, wherein only one mixing step is necessary between the active component and an inert aqueous dispersion of a polymer, and wherein no chemical or physical finishing treatment is necessary.

The active component thus retains a maximum of its activity, since no covalent binding to the polymer matrix is required.

In a preferred embodiment it was found that the best results were obtained by using an aqueous polyurethane dispersion as said aqueous dispersion of a polymer.

The above embodiment was found to be especially useful when said polypeptide is an enzyme such as glucose oxidase, catalase, or lactase.

The permeability modifying agent mentioned above is incorporated into the polymer matrix in order to control the permeability of the end product for small hydrophilic molecules, and it was found that use of various charged high molecular substances was successful.

Especially, when using a membrane of the invention for producing enzyme sensors, it is possible to control the permeability of various interfering substances by the addition of compounds such as heparin, alginic acid, or albumin.

Negatively charged substances such as heparin and alginic acid are especially useful for reducing the permeability of interfering anions, whereas neutral substances such as albumin are useful in controlling the permeability of the substance to be determined.

Although it is not necessary, it was found practical for obtaining membranes of a reasonable flexibility and avoiding formation of cracks to add a plasticizing agent to said aqueous dispersion in step a).

The plasticizer used may be any of the plasticizers normally used within the polymer industry, but for the purposes of this invention preferably dibutyl phthalate was used.

It was also found that the addition of a coalescence agent to said aqueous dispersion in step a) was of great use for the fusion (coalescence) of the individual particles in the dispersion.

Any suitable high boiling solvent well known to the practitioneer may be used, among such solvents ethyl carbitol, butyl carbitol, or N-methyl-2-pyrrolidone may be mentioned.

It was surprisingly found that it was possible to maintain the activity of enzymes immobilized within the polymeric matrix even when subjecting said dried shaped bodies to a mild heat treatment at a temperature of from about 40° C. to about 80° C. for a period of time of from about 30 minutes to about 30 hours.

Without being bound to any specific theory it is believed that said heat treatment improves the process by evaporating organics, such as the coalescence agent, and provides a smooth surface free of cracks or pores in the finished product.

It is also believed that this heat treatment has made it possible in contrast to other workers in the field to provide for a very high yield of functional membranes for use in biosensors.

Also, in the case of the production of a multi-layered membrane, it is believed that said heat treatment provides for a partial or full fusion of each separate layer to neighbouring layers.

In the preferred embodiment of the invention the subject membrane is advantageously applied by dip-coating, viz. the detecting surface of a biosensor, onto which the membrane must be applied, is carefully dipped into the above dispersion prior to the drying and optional heating steps.

The membrane may of course also be applied to a surface by spraying or any other conventional method of applying a coating (brushing, rolling, etc.).

By the invention there is also provided for a shaped body comprising a polypeptide, such as an enzyme immobilized in a polymer matrix, such as polyurethane.

Said shaped body may have any convenient form, but preferred are small beads and membranes, especially membranes.

In a further aspect the invention also provides for an electrochemical sensor comprising an anode, a cathode, and a detection surface, wherein said detection surface is coated with one or more layers of a membrane produced and applied by any of the above mentioned methods.

In a preferred embodiment of such a sensor said layer(s) are provided with one or more - outer - membranes of similar composition as said layers except for being devoid of any immobilized polypeptide or enzyme.

As a further feature by the invention it was found that sensors according to the invention could be sterilized easily by using a thiomersal containing test buffer during the conditioning period for the sensor.

EXAMPLE 1

MONO-LAYER NEEDLE ELECTRODE a) PHYSICAL CONSTRUCTION OF THE ELECTRODE

The electrode is shown in a longitudinal cross section in FIG. 1, and is generally designated 1. It comprises a core platinum anode 2 coated with an insulating lacquer 3, the anode 2 is situated inside a stainless steel reference cathode 4 which is insulated from the anode 2 by the lacquer 3 and a layer of epoxy resin 5. At one end, the tip, the electrode 1 has a detection surface 6, which is in an acute angle to the general direction of the electrode 1. At the other end, the base, the electrode 2 is provided with terminals 7 and 8 for the anode 2 and cathode 4, respectively. The terminals 7 and 8 are soldered to leads 9 and 10, respectively, which are connected to instrumentation used when performing measurements.

The electrode assembly is produced by inserting the commercially available lacquer insulated platinum wire 2, 3 with a diameter of 0.16 mm including the lacquer coating, into a stainless steel tube 4 with an outer diameter of 0.46 mm and finally the anode 2 is fixed in a nonconductive position in relation to the cathode 4 by embedding it in epoxy resin 5 inside the tube 4.

Working and reference electrodes 2 and 4 are subsequently at 7 and 8 soldered to the leads 9 and 10 of a low-loss or sub-miniature coaxial cable. All soldered connections are then embedded into epoxy resin.

Finally the electrode tip is ground to an angle of approximately 15 degrees and polished by honing the tip on a honing stone, whereby a smooth detection surface 6 level with the electrode tip, and an easy insertion of the electrode for in vivo measurements is obtained.

b) PRODUCTION AND APPLICATION OF AN ENZYME IMMOBILIZED IN A MEMBRANE

Mono-layer membranes were produced according to the following procedure:

The electrode assembly as produced by a) above is defatted and cleansed by piercing multiply folded lens tissue soaked in Ethyl Cellosolve ® 4 to 6 times, whereafter a potential of 650 mV is applied to the platinum anode 2, and the detection surface 6 dip-coated by dipping into the aqueous polymer dispersion of the invention to produce a coating A. The coating A is dried at room temperature while the detection surface 6 is kept in a horizontal position for a time sufficient for the current to decrease to at least 0.1 nA. Subsequent to this drying the coating A is subjected to a heat treatment at 45° C. for 24 hours.

Prior to use or testing the dry sensor 1 must be conditioned by immersing it into a buffer solution of for example the following composition

| TEST BUFFER | |
|---|---|
| $Na_2HPO_4 \cdot 2H_2O$ | 5.77 g |
| $NaH_2PO_4 \cdot H_2O$ | 1.05 g |
| Human albumin | 1.00 g |
| Thiomersal | 0.24 g |
| NaCl | 6.00 g |
| Demineralized water ad | 1000 ml |
| pH between 7.3 and 7.5 | | while a voltage of 650 mV is applied to the anode 2.

The sensor is deemed usable when a stable signal is generated. This typically is obtained within a period of from 5 to 24 hours. If it is impossible to obtain a stable signal within the specified period, the sensor is discarded.

As indicated above this conditioning also serves to sterilize the sensor through the activity of the thiomersal in the buffer solution. Experiments have shown that the thiomersal has no effect on the electrochemical characteristics of the biosensor.

c) TESTING OF SENSORS

Mono-layer electrodes produced as described above and with membrane compositions as indicated below were tested in an experimental set-up as outlined in FIG. 2.

In FIG. 2 a glucose containing sample buffer 11 is contained in a beaker 12. A sensor 1 is placed in a test stand 13 in a position where the detection surface 6 is immersed into the sample buffer, and the lead 9 from the anode 2 is connected to the positive terminal on a stabilized power supply 14 applying a voltage of 650 mV. The cathode 4 is connected to a current monitoring device 15, such as an amperometer, a recorder, or similar equipment through a cable 10. The monitor 15 and the power supply 14 are in turn connected through a cable 16.

In the actual set-up for the testing of the sensors of the invention the monitor 15 used was a Keithley picoamperometer Model 485, and the power supply 14 was an 1.5 V dry cell connected to a voltage divider.

MATERIALS

Polyurethane dispersion. A stock dispersion produced by incorporating 16 weight % dibutylphthalate (Merck-Schuchardt) in 84 weight % commercial polyurethane dispersion (NeoRez® R-974 from Polyvinyl Chemie Holland bv, Waalwijk, Holland), and adding an equal amount by weight of water.

Ethyl carbitol (Merck),

Sodium alginate. A stock solution of 2% (Sigma) in water was used.

Sodium heparin. A stock solution of 2% (NOVO INDUSTRI A/S) in water was used.

Glucose oxidase. A stock solution of 4.78 mg/ml (240 U pr. mg)(Serva).

TESTS

Tests were performed with mono-layer membranes produced from mixtures of the compositions indicated in Table I.

TABLE I

| Component | Amount | |
|---|---|---|
| | mix 1 | mix 2 |
| Polyurethane dispersion | 108 mg | |
| Polyurethane, pure NeoRez$^R$ R-970 | | 100 mg |
| Ethyl Carbitol | | 110 mg |
| Butyl Carbitol 10 weight % in water (demin.) | 921 mg | |
| Sodium alginate | | 100 mg |
| Glucose oxidase | 150 | 150 |
| Ferrocene aldehyde | | 5 mg |
| Water (demin.) | | 635 mg |

Two series of sensors were produced, one using mix 1 and designated sensor 1, was dried at room temperature for 24 hours, and the other using mix 2 and designated sensor 2, was heat treated at 60° C. for one hour.

From Table I it is seen that incorporation of ferrocene aldehyde in the polymer matrix was possible.

These mono-layer sensors were produced less effectively than the multi-layer sensors mentioned below in Example 2, since some had to be discarded due to instability.

Subsequent to conditioning the sensors were tested in the test buffer, to which aliquots of glucose was added to obtain concentrations of glucose in the buffer. The results from a testing of the above two mono-layer sensors are indicated in table II below.

TABLE II

|  | sensor 1 | sensor 2 |
| --- | --- | --- |
| Sensitivity (current) at 12 mM glucose | 5.9 nA |  |
| Sensitivity (current) at 10 mM glucose |  | 2.4 nA |
| Residual current at 0 mM glucose | <0.1 nA | <0.1 nA |
| Linear to at least (mM glucose) | 20 | 40 |
| Correlation coefficient (R) | 0.999 | 0.999 |

Sensor 2 was also tested in Vivo in a pig. The sensor was introduced in an ear vene through a Venflon® catheter. Blood samples were taken at intervals from the other ear and the glucose concentration measured by standard analysis in order to determine the correlation between the observed current in the sensor and the blood glucose content.

The result of this test was that the current in the sensor varied from 3 nA to 12 nA while the control varied from 2.4 mM glucose to 25 mM glucose. This shows that usually it is necessary to calibrate the sensor in situ prior to trusting the sensor measurements.

EXAMPLE 2

MULTI-LAYER NEEDLE ELECTRODE a) PHYSICAL CONSTRUCTION OF THE ELECTRODE

As shown in FIG. 3 the physical construction of multi-layer electrodes was identical to the mono-layer type except for the number of layers in the membrane.

b) PRODUCTION AND APPLICATION OF AN ENZYME IMMOBILIZED IN A MEMBRANE

The multi-layer membranes were produced according to the following procedure:

Each layer A, B, C, D shown in FIG. 3 is applied as for the mono-layer electrode except for the heat treatment which is only performed when the desired number of layers A, B, C, D has been applied.

The composition of the layers is usually identical except for one or two outermost layers which are devoid of enzyme.

Again the sensor must be conditioned prior to testing and/or use in the test buffer.

Tests

For this example two new mixtures were used, one without glucose oxidase for the outer layers in the membrane, and one containing glucose oxidase for the inner layers.

The compositions of the two mixtures are indicated in Table III below.

TABLE III

|  | Volume % | |
| --- | --- | --- |
| Component | mix 3 | mix 4 |
| polyurethane dispersion | 40 | 40 |
| Water (demin.) | 40 | 25 |

TABLE III-continued

|  | Volume % | |
| --- | --- | --- |
| Component | mix 3 | mix 4 |
| ethyl carbitol | 10 | 10 |
| sodium alginate | 10 | 10 |
| glucose oxidase |  | 15 |

From these mixtures one series of sensors was made comprising two inner layers from mix 4 and two outer layers from mix 3.

The layers were applied in a manner similar to that described in example 1, except that each individual layer was allowed to dry at room temperature for approximately 5 minutes prior to application of the next coating, and finally the four-layer membrane was heat treated at 65° C. for 45 minutes.

The structure of this four-layer needle sensor is shown in FIG. 3, where it is seen that in all other respects than the membrane A, B, C, D the structure is identical to the structure of the mono-layer sensor shown in FIG. 1.

Compared to the production of the mono-layer electrode the multi-layer electrodes proved more successful in respect of "yield" of usable electrodes.

Sensors from this production were similarly to example 1 tested for their response after conditioning. The results from this testing is shown in Table IV below

TABLE IV

| Sensitivity at 5 mM glucose | 1.5 nA +/−20% |
| --- | --- |
| Residual current at 0 mM glucose | <0.1 nA |
| Linear to at least (mM glucose) | 20* |
| Correlation coefficient (R) | 0.999 |

*The sensors were tested at 0, 2, 10, 15, and 20 mM glucose at 23 C.

LONG TERM STABILITY

A number of the sensors from this batch were tested for "long-term" stability by placing them in the test buffer containing 5 mM glucose at 23° C. and monitoring the result for at least 80 hours.

By this test it was found that the current varied less than 0.5% during this period.

PERMEABILITY CONTROL

In order to determine the dependency of the response from variations in alginate content a batch of sensors were produced wherein the membrane comprise two layers from mix 4 and two layers from mix 3 modified by substituting 100 µl sodium alginate solution with 10 µl sodium alginate solution plus 90 µl water.

The results from this test are shown in Table V below.

TABLE V

| Sensitivity at 5 mM glucose | 0.5 nA +/−20% |
| --- | --- |
| Residual current at 0 mM glucose | <0.1 nA |
| Linearity to at least (mM glucose) | 7* |
| Correlation coefficient (R) | 0.999 |

*The sensors were tested at 0, 5, and 7 mM glucose.

From Table V it is clearly seen that by reducing the alginate content in the membrane it was possible to reduce the sensitivity of the sensor by controlling the glucose permeability of the membrane.

I claim:

1. A method for producing a polyurethane membrane comprising an immobilized peptide, said method comprising:

a) adding (i) said polypeptide and (ii) a permeability modifying agent selected from the group consisting of heparin, alginic acid and albumin to an aqueous polyurethane dispersion wherein said polypeptide is dissolved;
b) shaping said aqueous dispersion into a membrane;
c) drying said polyurethane membrane whereby said polypeptide is entrapped in the polyurethane without any covalent bonding between the polypeptide and the polyurethane; and
d) optionally subjecting said dried polyurethane membrane to a heat treatment at a temperature of from about 40° C. to about 80° C. for a period of time of from about 30 minutes to about 30 hours.

2. The method according to claim 1, wherein said polypeptide is an enzyme.

3. The method according to claim 2, wherein said enzyme is a glucose oxidase, catalase or lactase.

4. The method according to claim 1, further comprising adding a plasticizing agent to said aqueous dispersion in step a).

5. The method according to claim 4, wherein said plasticizing agent is dibutyl phthalate.

6. The method according to claim 1, further comprising adding a coalescence agent to said aqueous dispersion in step a).

7. The method according to claim 6, wherein said coalescence agent is ethyl carbitol, butyl carbitol, or N-methyl-2-pyrrolidone.

8. A membrane wherein a polypeptide has been immobilized by physical entrapment in a polyurethane matrix comprising herapin, alginic acid or albumin without any covalent bonding between the polypeptide and the polyurethane.

9. The membrane according to claim 8, wherein said polypeptide is an enzyme.

10. The membrane according to claim 9, wherein said enzyme is glucose oxidase, catalase or lactase.

11. An electrochemical sensor comprising an anode, a cathode and a detection surface, wherein said detection surface is coated with one or more layers of a membrane according to claim 8.

12. The electrochemical sensor according to claim 11, wherein said layer(s) are provided with one or more outer-layer(s) of the same composition as said layers except for being devoid of the immobilized polypeptide.

* * * * *